United States Patent [19]
Steinbach et al.

[11] Patent Number: 6,156,349
[45] Date of Patent: Dec. 5, 2000

[54] METHOD OF TREATING HIV INFECTION WITH SUPPOSITORY CONTAINING MAMMALIAN LIVER EXTRACT

[75] Inventors: Thomas Steinbach, Houston; Phillip R. Pylant, Katy; William J. Hermann, Jr., Sealy, all of Tex.

[73] Assignee: Steinbach, Pylant and Herman, L.L.C., Sealy, Tex.

[21] Appl. No.: 09/210,393

[22] Filed: Dec. 14, 1998

[51] Int. Cl.[7] .................................................. A61K 35/407
[52] U.S. Cl. ............................ 424/553; 514/21; 514/885
[58] Field of Search .............................. 424/553; 514/21, 514/885; 530/846

[56] References Cited

U.S. PATENT DOCUMENTS

| | | | |
|---|---|---|---|
| 4,254,103 | 3/1981 | Timar | 424/106 |
| 4,883,660 | 11/1989 | Blackman et al. | 424/78 |
| 5,055,296 | 10/1991 | Wagle et al. | 424/553 |
| 5,284,664 | 2/1994 | Wagle et al. | 424/553 |
| 5,316,775 | 5/1994 | Wagle et al. | 424/553 |
| 5,334,395 | 8/1994 | Wagle et al. | 424/553 |
| 5,364,879 | 11/1994 | Herman | 514/452 |
| 5,492,937 | 2/1996 | Bogentoft et al. | 514/781 |
| 5,574,149 | 11/1996 | Van Tuttle et al. | 536/50 |
| 5,589,192 | 12/1996 | Okabe et al. | 424/486 |
| 5,595,760 | 1/1997 | Cherif-Cheikh | 424/464 |
| 5,725,864 | 3/1998 | Yamamoto et al. | 424/278.1 |

OTHER PUBLICATIONS

Chase, "Doctors and Patients Hope AZT Will Help Stave Off AIDS," *Wall Street Journal*, Apr. 28, 1988, pp. 1 and 19.

*Primary Examiner*—Jean C. Witz
*Attorney, Agent, or Firm*—Fitzpatrick, Cella, Harper & Scinto

[57] ABSTRACT

A method for treating human immuno-deficiency virus infection (HIV-1), comprising administering a therapeutically effective amount of a mammalian liver extract characterized by being heat stable, insoluble in acetone, and soluble in water. A rectal suppository colloidal dispersion delivery system for use in the treatment of HIV-1 infection further comprises an emulsion of resolubilized, concentrated mammalian liver extract.

13 Claims, No Drawings

METHOD OF TREATING HIV INFECTION WITH SUPPOSITORY CONTAINING MAMMALIAN LIVER EXTRACT

BACKGROUND OF THE INVENTION

1. Field of the Invention

The present invention is directed to a method of treating human immuno-deficiency virus (HIV-1) infections and to the discovery that a mammalian liver extract is efficacious in treating such infections. The present invention is also directed to a method of treating HIV-1 infections with this same mammalian liver extract. The present invention is further directed to a method of preparing a colloidal dispersion for use with this same mammalian liver extract. The present invention is also directed to a method of using a rectal suppository colloidal dispersion delivery system to treat HIV-1 infections.

2. Brief Description of Prior Art

Acquired immune deficiency syndrome (AIDS) and AIDS-related complex (ARC) are caused by human immuno-deficiency virus (HIV-1), a retrovirus. The HIV-1 virus infects immune, neural, and other cells of its host. Eventually most people infected with HIV-1 become abnormally susceptible to a variety of serious opportunistic diseases as a result of the immune deficiency caused by the virus.

The current anti-HIV-1 drugs are either not effective or cause undesirable side effects. These drugs include AZT, 2', 3'-dideoxy cytidine (ddCyd), interferon (IFN), mismatched double stranded RNA (dsRNA) and amphotericin B. In particular, AZT, which has shown some promise in the treatment of AIDS, causes very serious side effects, such as bone marrow suppression, in a high proportion of patients. Also, the beneficial effects of AZT have been reported to abate in 12–18 months, and patients get new infections or develop toxic side effects. (Chase, "Doctors and Patients Hope AZT Will Help Stave Off AIDS," *Wall Street Journal*, Apr. 28, 1988, p. 14, col. 1.)

One commercially available mammalian liver abstract useful for purposes of the present invention is sold under the trademark KUTAPRESSIN by Kremers-Urban Co., of Milwaukee, Wis. According to product literature, this extract exerts its action only with respect to tissues that have been injured, and particularly when inflammation and edema are present.

U.S. Pat. No. 5,055,296, filed by certain inventors common to the present application further discloses use of a particular heat stable, acetone-insoluble, water-soluble mammalian liver extract, designated as "KU 10,001" that was shown to be effective in the treatment of mammals infected with a non-dermatological virus and, in particular, chronic fatigue syndrome. The disclosure of this patent as to such extracts are incorporated herein by reference. This patent also discloses preliminary results of this extract as a protector of MT-2 cells using an in vitro test culture, when exposed to HIV-1.

U.S. Pat. No. 5,284,664, filed by certain inventors common to the present application, disclose a heat stable, acetone-insoluble, water-soluble mammalian liver extract, that is said to be effective in the treatment of symptoms of Alzheimer's Disease. The liver extract was also partially sequenced, and that sequence listing is incorporated herein by reference.

U.S. Pat. No. 5,316,775, filed by certain inventors common to the present application, discloses the same mammalian liver extract and demonstrates it to be effective in the treatment of Hepatitis B infections.

U.S. Pat. No. 5,334,395, filed by certain inventors common to the present application, discloses use of the same mammalian liver extract and demonstrates it to be effective in the treatment of Epstein-Barr viral infections.

U.S. Pat. No. 4,254,103, discloses a method of extracting Hepatoprotector Factor (HF) from bovine liver to be used in the treatment of cirrhosis of the liver and viral hepatitis.

U.S. Pat. No. 5,492,937, discloses a composition which is a liquid at or below room temperature, and forms a highly viscous gel at body temperature. This composition is comprised of a cellulose ether, a surfactant, and other optional additives. It may be used for oral or local administration of a pharmaceutical to the skin, mucous membrane, eye, or body cavity.

Against this background, the inventors have endeavored to discover a method to treat HIV-1 infections, using a heat stable, acetone-insoluble, water-soluble mammalian liver extract.

SUMMARY OF THE INVENTION

The present invention provides a method of treating HIV-1 infections involving administering to a mammal having said disease a therapeutically effective amount of mammalian liver extract, the extract being characterized by being heat stable, insoluble in acetone, and soluble in water, The terminology "heat stable" means that the liver extract does not lose appreciable activity at temperatures of about 100° C. in water over ten minutes. A preferred extract is specifically referred to as KUTAPRESSIN, which is further concentrated as disclosed herein. This invention also relates to a method of preparing a rectal suppository colloidal dispersion delivery system for use with said mammalian liver extract. This invention further relates to a method of using a rectal suppository colloidal dispersion delivery system to treat HIV-1 infections. One advantage of the above-mentioned colloidal dispersion delivery system is the improved ease of administration of the pharmaceutical composition by the patient. Another advantage of the above-mentioned colloidal dispersion delivery system is the ability to provide the pharmaceutical composition in a concentration high enough to be therapeutically effective in the treatment of HIV-1 infections.

Another advantage of the invention is the highly concentrated nature of the liver extract. The extracts of the prior art were more dilute and therefore administration of the liver extracts at dosages shown to be therapeutically effective herein for the treatment of HIV-1 viral infections was difficult and inefficient.

DETAILED DESCRIPTION OF PREFERRED EMBODIMENTS

The portion of mammalian liver extract that has been discovered to be effective in treating HIV-1 infection is the fraction which is heat stable, insoluble in acetone, and soluble in water. As disclosed in U.S. Pat. Nos. 5,284,664, 5,316,775, and 5,334,395, it is believed that these polysaccharides are present in KUTAPRESSIN in the form of proteoglycans or glycoproteins.

A rectal suppository has been discovered to be a particularly effective method of delivering a mammalian liver extract, such as KUTAPRESSIN, when further concentrated according to the present invention. A colloidal dispersion formulation allows the concentrated liver extract to be absorbed into the blood in concentrations apparently adequate for the treatment of HIV-1 infection.

PREPARATION OF A SUPPOSITORY DELIVERY SYSTEM FOR A COLLOIDAL DISPERSION OF KUTAPRESSIN

The rectal suppository colloidal dispersion employed in the present invention is the preferred method for administering the liver extract.

Dessicated liver extract is used to prepare the colloidal dispersion formulation. One way in which this may be accomplished is described below by dessicating 12 vials (240 ml) of commercially available KUTAPRESSIN. Four Nalgene dessicating systems are set up using calcium sulfate as the dessicating absorbant. Two evaporating dishes containing a total of three vials of KUTAPRESSIN are placed in each apparatus and a vacuum is applied via a pump for 7 minutes. The dessicating absorbant must be changed every 24 hours, and the vacuum pressure must be reapplied after each change of absorbant to restore the vacuum. After 72 hours, the liquid will be absorbed, leaving only active ingredient.

The desiccated KUTAPRESSIN is resolubilized in 16 to 18 ml of distilled water. Twelve drops of liquified phenol are then added to the resolubilized liver extract. One method of preparing the suppositories involves melting 40 g of polyglycol (MW 1450) with 20 g of polyglycol (MW 8000). Add the resolubilized KUTAPRESSIN to the melted polyglycol bases and mix well. Then quickly pour the KUTAPRESSIN colloidal dispersion into suppository molds, and refrigerate for approximately 1 hour. The end product is 30 suppositories, each containing 200 mg of KUTAPRESSIN. It is anticipated that other suppository delivery systems may be used to prepare the suppositories, without altering the effectiveness of the liver extracts of the present invention.

ADMINISTRATION OF LIVER EXTRACT

An acetone-insoluble liver extract useful in the present invention preferably is administered by suppository. However, other forms of administration are contemplated.

The liver extract may be employed in the form of pharmaceutically acceptable salts of the components, such as alkali metal salts. The pharmaceutically acceptable amides, lower alkyl esters, protected derivatives, other derivatives and analogs of the components of the liver extract are also contemplated.

While a rectal suppository containing the colloidal dispersion formulation is preferred, other pharmaceutical carriers, for example, a saline solution, could be employed. The liver extract preferably is administered as a suppository inserted into the rectum, while contained in a colloidal dispersion. A preferred product is a suppository containing the colloidal dispersion comprised of any of a variety of transdermal delivery vehicles and penetration enhancers containing KUTAPRESSIN which has been concentrated to a level of about 50 mg/ml. The use of a variety of transdermal delivery vehicles and penetration enhancers, as well as iontophoretic and phonophoretic methods of introducing KUTAPRESSIN transdermally, are also contemplated.

Dosages may vary depending upon the condition of the patient. Generally, however, it has been found that the administration of 400 mg of KUTAPRESSIN per day will produce beneficial results in as little as about 4 weeks.

CLINICAL OBSERVATION EXAMPLE 1

Two patients infected with HIV-1 received 400 mg of KUTAPRESSIN in the form of a suppository daily. Administration of the suppository containing the colloidal dispersion composition was begun after Quantitative HIV RNA PCR analysis was used to determine the number of HIV RNA copies per ml of each patient's blood. (See Table 1)

After receiving 400 mg of KUTAPRESSIN daily for 55 days in the form of a suppository inserted into the rectum, quantitative HIV RNA PCR analysis was used to determine each patient's HIV RNA level. (See Table 1)

TABLE 1

|  | Initial Copies of HIV RNA per ml | Copies of HIV RNA per ml after 55 Days of Treatment |
|---|---|---|
| Patient 1 | 8368 | 5491 |
| Patient 2 | 6726 | 1774 |

Although the invention has been described previously in connection with special and preferred embodiments, it will be understood that it is capable of modification without departing from the scope of the invention. The following claims are intended to cover all variations, uses, or adaptations of the invention which follow, in general, the principles thereof and including any departures from the present disclosure that are within known or customary practices in the field to which this invention pertains, or as are obvious to persons of ordinary skill in the field.

We claim:

1. A method for treating HIV-1 infections comprising administering to a mammal having said infection a therapeutically effective amount of a suppository containing a mammalian liver extract, the extract being heat stable, insoluble in acetone, and soluble in water, and wherein said mammalian liver extract is present in said suppository in concentrated form and substantially at least about 400 mg of the mammalian liver extract thereby is administered daily.

2. The method of claim 1, wherein the mammalian liver extract is a porcine liver extract.

3. The method of claim 1, wherein the mammalian liver extract is contained in a pharmaceutically acceptable colloidal dispersion formulation at a concentration of about 50 mg/ml.

4. The method of claim 2, wherein the porcine liver extract is contained in a pharmaceutically acceptable colloidal dispersion formulation at a concentration of about 50 mg/ml.

5. The method of claim 2, wherein about 400 mg of the porcine liver extract is administered daily.

6. A method of preparing a composition for the treatment of an HIV-1 infection in a mammal, comprised of:

a suppository delivery system; and a therapeutically effective amount of a mammalian liver extract that is present in said suppository in concentrated form and substantially at least 400 mg of the mammalian liver extract thereby is administered daily.

7. The method of claim 6, wherein the mammalian liver extract is a porcine liver extract.

8. The method of claim 6, wherein the mammalian liver extract is present at a concentration of about 50 mg/ml.

9. A method of treating an HIV-1 infection in a mammal by administering a therapeutically effective amount of a composition comprised of:

a suppository delivery system; and a therapeutically effective amount of a mammalian liver extract that is present in said suppository in concentrated form and substantially at least 400 mg of the mammalian liver extract thereby is administered daily.

10. The method of claim 9, wherein the mammalian liver extract is a porcine liver extract.

11. The method of claim 9, wherein the suppository delivery system is comprised of polyglycols.

12. The method of claim 9, wherein the mammalian liver extract is present at a concentration of about 50 mg/ml.

13. The method of claim 9, wherein about 400 mg of the mammalian liver extract is administered daily.

* * * * *